US012691060B1

(12) United States Patent
Parisi et al.

(10) Patent No.: US 12,691,060 B1
(45) **Date of Patent: *Jul. 28, 2026**

(54) LIQUID ORAL FORMULATIONS OF NETUPITANT AND PALONOSETRON

(71) Applicant: Helsinn Healthcare SA, Lugano / Pazzallo (CH)

(72) Inventors: Davide Parisi, Como (IT); Stefano Frizzarin, Varese (IT); Flavio Fabiani, Basel (CH)

(73) Assignee: Helsinn Healthcare SA, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 19/337,921

(22) Filed: Sep. 24, 2025

Related U.S. Application Data

(63) Continuation of application No. 19/231,152, filed on Jun. 6, 2025, which is a continuation of application No. PCT/IB2023/063415, filed on Dec. 31, 2023.

(60) Provisional application No. 63/436,713, filed on Jan. 3, 2023.

(51) Int. Cl.

| | |
|---|---|
| ***A61K 9/10*** | (2006.01) |
| ***A61K 9/00*** | (2006.01) |
| ***A61K 9/08*** | (2006.01) |
| ***A61K 31/473*** | (2006.01) |
| ***A61K 31/496*** | (2006.01) |
| ***A61K 47/10*** | (2017.01) |
| ***A61K 47/12*** | (2006.01) |
| ***A61K 47/26*** | (2006.01) |
| ***A61K 47/36*** | (2006.01) |

(52) U.S. Cl.
CPC .............. *A61K 9/0095* (2013.01); *A61K 9/08* (2013.01); *A61K 9/10* (2013.01); *A61K 31/473* (2013.01); *A61K 31/496* (2013.01); *A61K 47/10* (2013.01); *A61K 47/12* (2013.01); *A61K 47/26* (2013.01); *A61K 47/36* (2013.01)

(58) Field of Classification Search
CPC ......... A61K 9/10; A61K 9/1078; A61K 9/113
See application file for complete search history.

(56) References Cited

U.S. PATENT DOCUMENTS

| | | | | |
|---|---|---|---|---|
| 8,951,969 B2 * | 2/2015 | Trento | ...................... | A61P 1/08 514/17.7 |
| 2016/0206610 A1 * | 7/2016 | Armer | .................... | A61K 9/008 |

FOREIGN PATENT DOCUMENTS

| | | | |
|---|---|---|---|
| WO | WO-2019203753 A2 * | 10/2019 | ......... A61K 31/4985 |
| WO | 2022/038528 A1 | 2/2022 | |
| WO | 2004/067005 A1 | 8/2024 | |

OTHER PUBLICATIONS

PCT/IB2023/063415, Notification of Transmittal of the International Search Report and the Written Opinion of the International Searching Authority, or the Declaration (Mar. 27, 2024).
Gilmore James et al: "Complementary Pharmacokinetic Profiles of Netupitant and Palonosetron Support the Rationale for Their Oral Fixed Combination for the Prevention of Chemotherapy-Induced Nausea and Vomiting", The Journal of Clinical Pharmacology, vol. 59, No. 4, Nov. 9, 2018 (Nov. 9, 2018), pp. 472-487.
Anonymous: "PK/PD Study of Netupitant and Palonosetron in Pediatric Patients for Prevention of Chemotherapy-induced Nausea and Vomiting (CINV)", Dec. 7, 2020 (Dec. 7, 2020) ClinicalTrials.gov [retrieved on Jun. 4, 2025].

* cited by examiner

*Primary Examiner* — Micah Paul Young
(74) *Attorney, Agent, or Firm* — Clark G. Sullivan

(57) ABSTRACT

Orally administered liquid formulations of netupitant and palonosetron, and suitable pharmaceutical excipients, in a solvent system that allows for the netupitant to be suspended and the palonosetron to be dissolved, that are efficacious, chemically stable and physiologically balanced for safety and efficacy.

21 Claims, No Drawings

LIQUID ORAL FORMULATIONS OF NETUPITANT AND PALONOSETRON

RELATIONSHIP TO PRIOR APPLICATIONS

This application is a continuation of U.S. Ser. No. 19/231,152, filed Jun. 6, 2025, which is a continuation of PCT/IB2023/063415, filed with the International Bureau of the World International Property Organization on Dec. 31, 2023, designating the United States, which claims priority to U.S. provisional application No. 63/436,713, filed Jan. 3, 2023.

FIELD OF INVENTION

The present disclosure relates to orally administered liquid formulations of netupitant and palonosetron that are efficacious, chemically stable, and physiologically balanced for safety and efficacy.

BACKGROUND OF INVENTION

Solutions and suspensions of drugs are used widely in the pharmaceutical industry as dosage forms for different routes of administration, including oral, parenteral and inhalation, but they are generally considered different dosage forms, and techniques needed to form a homogenous/readily dispensed suspension of a drug substance will differ from the techniques needed to form a pharmaceutically acceptable solution/suspension. For a detailed review of these techniques and other associated issues, the reader is referred for example to Remington, The Science and Practice of Pharmacy (current edition).

Generally speaking, the preparation of solutions and suspensions involves several considerations on the part of the manufacturer, including the purpose of the drug, internal or external use, solubility and concentration of the drug, selection of the liquid vehicle(s), physical and chemical stability of the drug and any excipients, preservation of the dosage form, and use of appropriate excipients such as buffers, solubility enhancers, suspending agents, emulsifying agents, viscosity controlling agents, colors and flavors. The viscosity of a product also must be considered so that it has the proper palatability for an oral preparation and has the appropriate suspending properties if it is an emulsion or suspension.

Bioavailability is also an important consideration and is greatly affected in solutions by factors including drug concentration, volume of liquid administered, pH, ionic strength, buffer capacity, surface tension, specific gravity, viscosity, and excipients. The bioavailability of emulsions and suspensions may be affected by other factors including surfactants, type of viscosity agent, particle size, particle size distribution, polymorphism, and solubility of the drug in an oil phase emulsion.

Dispensability is another important consideration. When dispensing from a single unit dosage form, such as a vial or stick pack, it is important to find a packaging material that allows the formulation to remain stable and that further permits nearly 100% of the housed formulation to be dispensed to the patient.

Combined dosage forms of netupitant and palonosetron are known. WO/2013/057554, for example, discloses a fixed dose combination of palonosetron hydrochloride and netupitant in an oral capsule for the prevention of chemotherapy induced nausea and vomiting ("CINV"). However, WO/2013/057554 does not describe a liquid formulation suitable for oral administration. Moreover, WO2013/057554 and other prior art do not disclose a liquid formulation suitable for oral administration in which netupitant or a pharmaceutically acceptable salt thereof and palonosetron or pharmaceutically acceptable salt thereof are contained together, in a single unit dosage form.

It is an object of the present disclosure to define liquid oral dosage forms of netupitant and palonosetron, and regimens for the prevention of CINV using such dosage forms, including in pediatric patients.

SUMMARY OF THE INVENTION

In one embodiment the disclosure provides an orally administered antiemetic composition in a mixed suspension/solution solvent system comprising palonosetron or a pharmaceutically acceptable salt thereof and netupitant or a pharmaceutically acceptable salt thereof together in a liquid single unit dosage form.

In one embodiment the disclosure provides an orally administered antiemetic composition in a mixed suspension/solution solvent system comprising palonosetron or a pharmaceutically acceptable salt thereof in a dissolved state and netupitant or a pharmaceutically acceptable salt thereof in a solid suspended state, together in a liquid single unit dosage form.

In another embodiment the disclosure provides an orally administered antiemetic composition in a mixed suspension/solution solvent system comprising: (a) from 0.01 to 0.2 mg/mL palonosetron or a pharmaceutically acceptable salt thereof (based on the weight of the free base) in a dissolved state and from 10 to 100 mg/mL of netupitant or a pharmaceutically acceptable salt thereof (based on the weight of the free base) in a solid suspended state, preferably wherein the netupitant or pharmaceutically salt thereof has a particle size distribution defined by a d(50) of 1-8 μm and a d(90) of not more than 24 μm or a d(50) of 2-4 μm and a d(90) of not more than 12 μm, and (b) a solvent system in which the netupitant or pharmaceutically salt thereof is insoluble but homogenously suspended and the palonosetron or pharmaceutically acceptable salt thereof is soluble. In another embodiment the solvent system comprises water, one or more miscibilized wetting agents, one or more miscibilized suspending agents, one or more miscibilized pH modifiers optionally one or more miscibilized sweetening agents, and optionally one or more miscibilized preservatives.

In one embodiment particularly suitable for adult administration the formulation is present in a unit dose package comprising 300 mg of netupitant or a pharmaceutically acceptable salt thereof at a concentration of 30 mg/mL, and 0.5 mg of palonosetron or a pharmaceutically acceptable salt thereof at a concentration of 0.05 mg/mL, wherein the doses and concentrations are based on the free form of the netupitant and palonosetron. Thus, if the formulation contains palonosetron HCl, 0.56 mg of palonosetron HCl will be present at a concentration of 0.056 mg/mL.

In one embodiment particularly suitable for adult administration the formulation is present in a unit dose package comprising about 300 mg of netupitant or a pharmaceutically acceptable salt thereof preferably at a concentration of 60 mg/mL, and about 0.5 mg of palonosetron or a pharmaceutically acceptable salt thereof preferably at a concentration of 0.1 mg/mL, wherein the doses and concentrations are based on the free form of the netupitant and palonosetron. Thus, if the formulation contains palonosetron HCl, 0.56 mg of palonosetron HCl will be present at a concentration of 0.112 mg/mL.

In one embodiment particularly suitable for pediatric administration the formulation is present in a unit dose package comprising about 300 mg of netupitant or a pharmaceutically acceptable salt thereof preferably at a concentration of 30 mg/mL, and about 1.5 mg of palonosetron or a pharmaceutically acceptable salt thereof preferably at a concentration of 0.15 mg/mL, wherein the doses and concentrations are based on the free form of the netupitant and palonosetron. Thus, if the formulation contains palonosetron HCl, 1.68 mg of palonosetron HCl will be present at a concentration of 0.168 mg/mL.

In another embodiment the palonosetron is palonosetron HCl.

In one embodiment, the one or more pH modifiers help to ensure the stability of palonosetron or pharmaceutically acceptable salt thereof providing a good uniformity of the liquid formulation in which also the netupitant or pharmaceutically acceptable salt thereof is contained.

In another embodiment, the one or more miscibilized suspending agents such as the xanthan gum provide that the composition does not present sedimentation and/or separation phenomena during storage. In another embodiment, the one or more miscibilized suspending agent such as the xanthan gum increase the viscosity, thus decreasing or avoiding sedimentation.

In one embodiment, the disclosure provides an orally administered antiemetic composition in which, despite their different solubility characteristics, the palonosetron or pharmaceutically acceptable salt thereof and the netupitant or pharmaceutically acceptable salt thereof are contained together, in a single and stable combination in a liquid formulation. Accordingly, palonosetron or a pharmaceutically acceptable salt thereof is contained in a dissolved state and netupitant or a pharmaceutically acceptable salt thereof is contained in a solid suspended state and both are together in the mixed suspension/solution solvent system. In a preferred embodiment, the orally administered antiemetic composition as above is an oral suspension. It was surprisingly found that palonosetron or a pharmaceutically acceptable salt thereof and netupitant or a pharmaceutically acceptable salt thereof formulated according to the mixed suspension/solution solvent system of the current disclosure remain stable in the liquid formulation, without sedimentation.

In one embodiment, having the palonosetron or pharmaceutically acceptable salt thereof in a dissolved form in the solution guarantees homogeneity even with low dosages of the active ingredient.

In another embodiment the disclosure provides a unit dose packaged composition comprising: (a) a unit dose package selected from a pouch (e.g. a stick pack or sachet), a plastic vial, a plastic tube, and a glass vial; (b) from 0.01 to 0.2 mg/mL palonosetron or a pharmaceutically acceptable salt thereof (based on the weight of the free base) in a dissolved state and from 10 to 100 mg/mL of netupitant or a pharmaceutically acceptable salt thereof (based on the weight of the free base) in a solid suspended state, preferably wherein the netupitant or pharmaceutically salt thereof has a particle size distribution defined by a d(50) of 1-8 μm and a d(90) of not more than 24 μm or a d(50) of 2-4 μm and a d(90) of not more than 12 μm.; and (c) a solvent system in which the netupitant or pharmaceutically acceptable salt thereof is insoluble and the palonosetron or pharmaceutically salt thereof is soluble comprising water, one or more miscibilized wetting agents, one or more miscibilized suspending agents, one or more pH modifiers optionally one or more miscibilized sweetening agents, and optionally one or more miscibilized preservatives.

Another embodiment provides a method of preventing chemotherapy induced nausea and vomiting in a human patient in need thereof comprising orally administering to the patient an antiemetic composition in a mixed suspension/solution solvent system comprising palonosetron or a pharmaceutically acceptable salt thereof and netupitant or a pharmaceutically acceptable salt thereof together in a single liquid dosage form.

Another embodiment provides a method of preventing chemotherapy induced nausea and vomiting in a human patient in need thereof comprising orally administering to the patient about 300 mg of netupitant or pharmaceutically acceptable salt thereof (based on the weight of the free base) and about 0.5 mg palonosetron or pharmaceutically acceptable salt thereof (based on the weight of the free base) from a composition of the present disclosure.

Another embodiment provides a method of preventing chemotherapy induced nausea and vomiting in a human pediatric patient in need thereof comprising orally administering to the patient about 300 mg of netupitant or pharmaceutically acceptable salt thereof and about 1.5 mg palonosetron or pharmaceutically acceptable salt thereof from a composition of the present disclosure.

In another embodiment the invention provides a method of manufacturing an orally administered antiemetic composition in a mixed suspension/solution solvent system comprising: (a) making a bulk formulation comprising from 0.01 to 0.2 mg/mL palonosetron or a pharmaceutically acceptable salt thereof (based on the weight of the free base) in a dissolved state and from 10 to 100 mg/mL of netupitant or a pharmaceutically acceptable salt thereof (based on the weight of the free base) in a solid suspended state; and (b) filling the bulk formulation into a plurality of unit dose packages while continuously stirring the formulation to minimize or prevent foaming.

Another embodiment provides the palonosetron as palonosetron HCl.

Additional advantages of the disclosure are set forth in part in the description that follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Definitions and Use of Terms

Throughout this application, various publications are referenced. The disclosures of these publications in their entireties are hereby incorporated by reference into this application in order to more fully describe the state of the art to which this disclosure pertains. The references disclosed are also individually and specifically incorporated by reference herein for the material contained in them that is discussed in the sentence in which the reference is relied upon.

As used in the specification and claims, the singular forms a, an, and the include plural references unless the context clearly dictates otherwise. For example, the term "a pharmaceutical excipient" refers to one or more pharmaceutical excipients for use in the presently disclosed formulations and methods.

When ranges are given by specifying the lower end of a range separately from the upper end of the range, it will be understood that the range can be defined by selectively combining any one of the lower end variables with any one of the upper end variables that is mathematically possible.

When used herein the term "about" will compensate for variability allowed for in the pharmaceutical industry and inherent in pharmaceutical products, such as differences in product strength due to manufacturing variation and time-induced product degradation. In one embodiment the term allows for any variation which in the practice of pharmaceuticals would allow the product being evaluated to be considered pharmaceutically equivalent or bioequivalent to the recited strength. In another embodiment the term allows for any variation within 5% of the recited strength or concentration of the formulation.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts that are pharmaceutically acceptable, as defined above, and which possess the desired pharmacological activity. It will be understood that the salt can disassociate in a liquid medium into ion/counter-ion pairs, and still constitute a "salt" as that term is used in the present document according to industry custom.

Exemplary salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

When a weight of an active ingredient is given without reference to the free base or salt of the active ingredient, it will be understood that the weight can refer to the weight of the free base or the weight or the entire salt. In like manner, when the molecule can exist as a hydrate, and the weight of the molecule is given, it will be understood that the weight can be refer to the weight of the hydrate or the weight of the molecule without the waters of hydration.

When an ingredient is expressed based on its percentage, such as sorbitol 70% n.c., it will be understood to refer to any combination of sorbitol and water that produces 70% sorbitol. Thus, if a formulation comprises sorbitol 70% n.c., it will be understood that 7 parts anhydrous sorbitol (100%) can be combined with 3 parts water in the formulation to produce the sorbitol 70% n.c.

"Disodium edetate" or "EDTA" refers to anhydrous disodium edetate or any of its hydrated forms. In one embodiment the compositions of the disclosure lack EDTA.

The term "liquid formulation" or "liquid solution" or "liquid suspension" or words of similar import refers to a liquid formulation that is suitable for therapeutic administration. The formulation can be manufactured as a liquid and packaged as such.

"Netupitant" refers to 2-(3,5-bis(trifluoromethyl)phenyl)-N,2-dimethyl-N-(6-(4-methylpiperazin-1-yl)-4-(o-tolyl)pyridine-3-yl)propanamide. The compound has the following chemical structure:

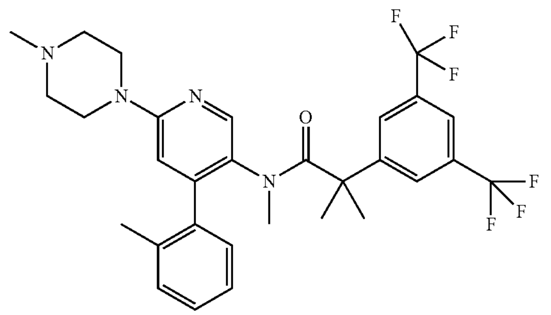 [SMILES: Cc1ccccc1-c1cc(N2CCN(C)CC2)ncc1N(C)C(=O)C(C)(C)c1cc(C(F)(F)F)cc(C(F)(F)F)c1]

The netupitant is preferably micronized. By laser diffraction, the particle size is preferably d(50) of 2-4 μm and d(90) of not more than 12 μm.

"Palonosetron" refers to (3aS)-2-[(S)-1-azabicyclo[2.2.2]oct-3-yl]-2,3,3a,4,5,6-hexahydro-1-oxolHbenz[de]isoquinoline having a molecular weight of 296.407. The hydrochloride salt has a molecular weight of 332.87 and the following chemical structure:

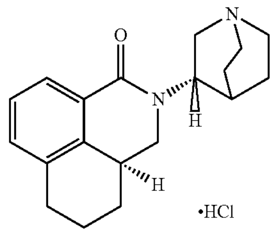 [SMILES: O=C1c2cccc3c2[C@H](CCC3)CN1[C@@H]1CN2CCC1CC2 ; Cl]

Thus, a formulation that contains 0.5 mg of palonosetron HCl based on the weight of the free form of palonosetron will contain 0.56 mg of palonosetron HCl.

The term "pediatric" refers to a human subject less than 18 years of age, including human subjects less than 12, 8, and 6 years of age, including human subjects from 3-12 and from 3-18 years of age.

"Mixed suspension/solution solvent system" refers to a liquid formulation in which one agent is present in its dissolved state and another agent is present in its suspended state together in the same formulation.

For the sake of clarity, it will be understood that, for regulatory or marketing purposes, a mixed suspension/solution solvent system can be classified and/or marketed simply as a "suspension." It will be understood that a formulation marketed as a "suspension" would still qualify as a "mixed suspension/solution solvent system," as long as one agent is present in its dissolved state and another agent is present in its suspended state together in the same formulation.

The terms "reducing sugar" and "total sugar" when used herein have the meaning ascribed to them by the United States Pharmacopoeia USP 37-NF 32 and as generally understood by workers of ordinary skill in the art.

Discussion

In one embodiment the disclosure provides an orally administered antiemetic composition in a mixed suspension/solution solvent system comprising palonosetron or a pharmaceutically acceptable salt thereof and netupitant or a pharmaceutically acceptable salt thereof together in a single liquid dosage form.

In another embodiment the disclosure provides an orally administered antiemetic composition in a mixed suspension/solution solvent system comprising: (a) from 0.01 to 0.2 mg/mL palonosetron or a pharmaceutically acceptable salt thereof (based on the weight of the free base) in a dissolved state and from 10 to 100 mg/mL of netupitant or a pharmaceutically acceptable salt thereof (based on the weight of the free base) in a solid suspended state, preferably wherein the netupitant or pharmaceutically salt thereof has a particle size distribution defined by a d(50) of 1-8 μm and a d(90) of not more than 24 μm or a d(50) of 2-4 μm and a d(90) of not more than 12 μm; and (b) a solvent system in which the netupitant or pharmaceutically acceptable salt thereof is insoluble but homogenously suspended and the palonosetron or pharmaceutically acceptable salt thereof is soluble. In another embodiment, the solvent system of point (b) comprises water, one or more miscibilized wetting agents, one or more miscibilized suspending agents, one or more miscibilized pH modifiers, optionally one or more miscibilized sweetening agents, and optionally one or more miscibilized preservatives. In one embodiment, the palonosetron is palonosetron HCl.

In another embodiment the disclosure provides a unit dose packaged composition comprising: (a) a unit dose package selected from a pouch (e.g. a stick pack or sachet), a plastic vial, a plastic tube, and a glass vial; (b) from 0.01 to 0.2 mg/mL palonosetron or a pharmaceutically acceptable salt thereof (based on the weight of the free base) in a dissolved state and from 10 to 100 mg/mL of netupitant or a pharmaceutically acceptable salt thereof (based on the weight of the free base) in a solid suspended state, preferably wherein the netupitant or pharmaceutically salt thereof has a particle size distribution defined by a d(50) of 1-8 μm and a d(90) of not more than 24 μm or a d(50) of 2-4 μm and a d(90) of not more than 12 μm; and (c) a solvent system in which the netupitant or pharmaceutically acceptable salt thereof is insoluble and the palonosetron or pharmaceutically salt thereof is soluble. In another embodiment, the solvent system of (c) above comprises water, one or more miscibilized wetting agents, one or more miscibilized suspending agents, one or more pH modifiers, optionally one or more miscibilized sweetening agents, and optionally one or more miscibilized preservatives.

Another embodiment provides a method of preventing chemotherapy induced nausea and vomiting in a human patient in need thereof comprising orally administering to the patient an antiemetic composition in a mixed suspension/solution solvent system comprising palonosetron or a pharmaceutically acceptable salt thereof and netupitant or a pharmaceutically acceptable salt thereof together in a single liquid dosage form.

Another embodiment provides a method of preventing chemotherapy induced nausea and vomiting in a human patient in need thereof comprising orally administering to the patient about 300 mg of netupitant or pharmaceutically acceptable salt thereof (based on the weight of the free base) and about 0.5 mg of palonosetron or a pharmaceutically acceptable salt thereof (based on the weight of the free base) from a composition of the present disclosure.

Another embodiment provides a method of preventing chemotherapy induced nausea and vomiting in a human pediatric patient in need thereof comprising orally administering to the patient about 300 mg of netupitant or a pharmaceutically acceptable salt thereof (based on the weight of the free base) and about 1.5 mg palonosetron or a pharmaceutically acceptable salt thereof (based on the weight of the free base) from a composition of the present disclosure.

In one embodiment the palonosetron is present as palonosetron HCl and the netupitant is present as the free base. In another embodiment the netupitant is present as a free base and has a particle size distribution defined by a d(50) of 2-4 μm and a d(90) of not more than 12 μm.

In one embodiment the compositions of the present disclosure have a pH of from 4 to 7. In another embodiment the compositions of the present disclosure have a pH of from 5 to 6. In one embodiment these pH values, and preferably a pH ranging from 5 to 6, provide the compositions of the present disclosure with a rheological profile that is thixotropic avoiding sedimentation and/or separation of the compositions during the storage.

In some embodiments the density of the formulation is from 1.1-1.3 mg/mL. In one embodiment the density is from 1.15 to 1.28 mg/mL. In another embodiment, the density is from 1.18 to 1.26 mg/mL.

The formulation is preferably an aqueous-based formulation, with the ingredients combined and dissolved in water. The formulation can be isotonic or non-isotonic. The formulation can optionally be 5 mL or 10 mL for adult or pediatric administration.

In one embodiment, particularly well adapted to a 10 mL adult formulation, the composition of the present disclosure comprises 30 mg/mL of netupitant free base and 0.056 mg/mL of palonosetron HCl. In another embodiment, particularly well adapted to a 5 mL adult formulation, the composition the composition of the present disclosure comprises 60 mg/mL of netupitant free base and 0.112 mg/mL of palonosetron HCl. In another embodiment, particularly well adapted to a 10 mL pediatric formulation, the composition of the present disclosure comprises 30 mg/mL of netupitant free base and 0.168 mg/mL of palonosetron HCl.

Formulations can also be defined based on ranges of concentrations of netupitant and palonosetron, or pharmaceutically acceptable salts thereof, in the formulation. In one embodiment particularly suitable for adults (particularly when the unit dose is 10 mL) the composition comprises: (a) from 20 to 40 mg/mL, from 25 to 35 mg/mL, or 30 mg/mL netupitant or a pharmaceutically acceptable salt thereof (based on the weight of the free base); and (b) from 0.02 to 0.08 mg/mL, from 0.03 to 0.07 mg/mL, or 0.05 mg/mL palonosetron or a pharmaceutically acceptable salt thereof (based on the weight of the free base). In another embodiment particularly suitable for adults (particularly when the unit dose is 5 mL) the composition comprises: (a) from 40 to 80 mg/mL, from 50 to 70 mg/mL, or 60 mg/mL netupitant or a pharmaceutically acceptable salt thereof (based on the weight of the free base); and (b) from 0.05 to 0.15 mg/mL, from 0.075 to 0.125 mg/mL, or 0.1 mg/mL palonosetron or a pharmaceutically acceptable salt thereof (based on the weight of the free base). In another embodiment particularly suitable for pediatrics (particularly when the unit dose is 10 mL) the formulations of the present disclosure comprise from 20 to 40 mg/mL, from 25 to 35 mg/mL, or 30 mg/mL netupitant or a pharmaceutically acceptable salt thereof (based on the weight of the free base), and from 0.1 to 0.2 mg/mL, from 0.125 to 0.175 mg/mL, or 0.15 mg/mL palonosetron or a pharmaceutically acceptable salt thereof (based on the weight of the free base).

In one embodiment a unit dose package for adult administration will comprise 300 mg of netupitant or a pharmaceutically acceptable salt thereof at a concentration of 30 mg/mL, and 0.5 mg of palonosetron or a pharmaceutically acceptable salt thereof at a concentration of 0.05 mg/mL, wherein the doses and concentrations are based on the free form of the netupitant and palonosetron.

In one embodiment a unit dose package for adult administration will comprise 300 mg of netupitant or a pharmaceutically acceptable salt thereof at a concentration of 60 mg/mL, and 0.5 mg of palonosetron or a pharmaceutically acceptable salt thereof at a concentration of 0.1 mg/mL, wherein the doses and concentrations are based on the free form of the netupitant and palonosetron.

In another embodiment a unit dose package for pediatric administration will comprise 300 mg of netupitant or a pharmaceutically acceptable salt thereof at a concentration of 30 mg/mL, and 1.5 mg of palonosetron or a pharmaceutically acceptable salt thereof at a concentration of 0.15 mg/mL, wherein the doses and concentrations are based on the free form of the netupitant and palonosetron.

The formulations of the present disclosure can be further defined in terms of inactive ingredients. In some embodiments, the wetting agent used in the formulations of the present disclosure is selected from the group consisting of glycerin, propylene glycol, polyethylene glycol, ethanol, and combinations thereof.

In some embodiments, the wetting agent is glycerin, and the formulation comprises from 25 to 100 mg/mL, from 35 to 75 mg/mL, or 50 mg/mL glycerin.

In some embodiments, the suspending agent is selected from the group consisting of cellulose derivatives, acacia, xanthan gum, and combinations thereof. In some embodiments the suspending agent comprises xanthan gum, and the formulation comprises xanthan gum in an amount of from 2.5 to 3.5 mg/mL, from 2.75 to 3.25 mg/mL, or 3 mg/mL. The suspending agent xanthan gum is stickier with respect to formulations containing other thickening agents, but this feature does not affect the dosing operation. The preparations containing xanthan gum are the most physically stable. According to the present disclosure, formulations comprising xanthan gum as a suspending agent are also characterized by a quick and complete hydration of the polymer that allows a rapid and simple manufacturing process. On the contrary, for example, cellulose used as suspending agent shows separation (sedimentation) after about 30 days of storage and formulations containing carboxymethyl cellulose show separation after 20 days. The formulations of the present disclosure comprising xanthan gum remain stable and show absence of sedimentation also after 30 days storage at room temperature, demonstrating the desired stability.

In some embodiments, the formulations of the current disclosure include a sweetening agent, and the sweetening agent is a monosaccharide selected from the group consisting of glucose, fructose, galactose, and combinations thereof, or a sugar alcohol selected from the group consisting of ethylene and or propylene glycol; glycerol; erythritol; threitol; arabitol; xylitol; ribitol; mannitol; sorbitol; galactitol; fucitol; iditol; inositol; volemitol; isomalt; maltitol; lactitol; maltotriitol; maltotetraitol; polyglycitol; and combinations thereof. In some embodiments, the formulations of the current disclosure comprise sorbitol as sweetening agent. Sorbitol shows a better stability performance in the formulations of the current disclosure, in comparison for example to sucrose syrup that gives a high range of viscosity leading to less stability.

In some embodiments the formulation will comprise from 800 mg/mL to 950 mg/mL, from 850 to 900 mg/mL, or 886.333 mg/mL sorbitol syrup n.c. 70%. The sorbitol is in one embodiment of the non-crystallizing type.

When sorbitol syrup or another form of sorbitol is employed in the formulation, various embodiments can be defined based on the ratio of water to sorbitol in the overall formulation, or the ratio of water to sorbitol to netupitant in the overall formulation. Thus, in various embodiments the formulation comprises: from 20 to 60 wt % water and from 30 to 70 wt % sorbitol, or from 30 to 50% water and from 40 to 60% sorbitol. In other embodiments the formulation comprises from 20 to 60 wt % water and from 30 to 70 wt % sorbitol and from 1.5 to 4.0% netupitant, or from 30 to 50% water and from 40 to 60% sorbitol and from 2.0 to 3.0% netupitant.

Of course, it will be understood that sorbitol is but one sweetener among many which could be used in the formulations of the present invention. Thus, in some embodiments, the formulation comprises one or more sweetening agents, preferably a monosaccharide selected from the group consisting of glucose, fructose, galactose, and combinations thereof, and/or a sugar alcohol selected from the group consisting of ethylene and or propylene glycol; glycerol; erythritol; threitol; arabitol; xylitol; ribitol; mannitol; sorbitol; galactitol; fucitol; iditol; inositol; volemitol; isomalt; maltitol; lactitol; maltotriitol; maltotetraitol; polyglycitol; and combinations thereof.

The above mentioned sweeteners may contain reducing sugars as residuals substances, remaining from the synthesis process. These reducing sugars, and/or their degradation products, could be highlighted in the Drug Product analysis, with the risk to be classified as "unknown" impurities, with a limit of Not More Than (NMT) 0.2% to avoid having to assess the structure of the impurities and determine their toxicity. Thus, in another embodiment, the formulation comprises no more than 0.2% reducing sugars based on the total weight of the sweetener.

Sorbitol is considered one of the most diffuse sweeteners. Limits on reducing sugars for sorbitol are reported in the USP and Ph. Eur. as 0.3% and 0.2%, respectively all the amounts can be detected as "unknown" impurity, being the same reducing sugar or one of its degradation products. Thus, in another embodiment, the formulation comprises no more than 0.3% or 0.2% sorbitol reducing sugars based on the weight of the sorbitol.

To avoid, or minimize, the presence of those impurities, the sweetening agents (particularly sorbitol) will in one embodiment contain a very low amount of reducing sugars relative to the limits reported in the USP and Ph. Eur., and in one embodiment the sweetening agent (particularly sorbitol) comprises no more than 0.05% reducing sugars and no more than 0.25% total sugar based on the weight of the sucrose.

In some embodiments the compositions of the present disclosure comprise a preservative selected from the group consisting of parabens, alcohol, glycerin, propylene glycol, sorbates, and combinations thereof. In other embodiments, the compositions of the present disclosure comprise potassium sorbate, in a concentration of from 0.5 to 1.5 mg/mL, from 0.75 to 1.25 mg/mL, or 1 mg/mL.

In some embodiments, the compositions of the present disclosure comprise a pH modifier selected from the group consisting of citric acid anhydrous and sodium citrate tribasic and combinations thereof.

In one embodiment the disclosure provides formulations comprising a combination of inactive excipients comprising (a) from 25 to 100 mg/mL, from 35 to 75 mg/mL, or 50 mg/mL glycerin; and (b) from 2 to 4 mg/mL, from 2.5 to 3.5 mg/mL, or 3 mg/mL xanthan gum.

In other embodiments the disclosure provides formulations comprising a combination of inactive excipients comprising from 2 to 4 mg/mL, from 2.5 to 3.5 mg/mL, or 3 mg/mL xanthan gum, from 800 mg/mL to 950 mg/mL, from 850 to 900 mg/mL, or 886.333 mg/mL sorbitol syrup n.c. 70%, and from 0.5 to 1.5 mg/mL, from 0.75 to 1.25 mg/mL, or 1 mg/mL potassium sorbate.

In another embodiment the disclosure provides formulations comprising a combination of inactive excipients comprising from 2 to 4 mg/mL xanthan gum, from 800 to 950 mg/mL sorbitol syrup n.c. 70%, and from 0.5 to 1.5 mg/mL potassium sorbate.

In another embodiment the disclosure provides formulations comprising a combination of inactive excipients comprising from 2.5 to 3.5 mg/mL xanthan gum, from 850 to 900 mg/mL sorbitol syrup n.c. 70%, and from 0.75 to 1.25 mg/mL potassium sorbate.

Alternatively, the formulations can be described in terms of active and inactive ingredients. Thus, in one embodiment particularly suitable for a 10 mL adult formulation the formulations of the current disclosure comprise from 25 to 35 mg/mL netupitant or a pharmaceutically acceptable salt thereof (based on the weight of the free base), from 0.025 to 0.075 mg/mL palonosetron or a pharmaceutically acceptable salt thereof (based on the weight of the free base), from 2 to 3 mg/mL xanthan gum, from 800 to 950 mg/mL sorbitol syrup n.c. 70%, and from 0.5 to 1.5 mg/mL potassium sorbate.

In another embodiment particularly suitable for a 10 mL adult formulation the formulations comprise from 25 to 35 mg/mL netupitant or a pharmaceutically acceptable salt thereof (based on the weight of the free base), from 0.025 to 0.075 mg/mL palonosetron or a pharmaceutically acceptable salt thereof (based on the weight of the free base), from 2.5 to 3.5 mg/mL xanthan gum, from 850 to 900 mg/mL sorbitol syrup n.c. 70%, and from 0.75 to 1.25 mg/mL potassium sorbate.

In one embodiment particularly suitable for a 10 mL adult formulation the composition comprises: (a) 30 mg/mL netupitant free base; (b) 0.05 mg/mL palonosetron HCl; (c) 50 mg/mL glycerin 98%; (d) 3 mg/mL xanthan gum; (e) 2 mg/mL citric acid anhydrous as a pH modifier; (f) 13.75 mg/mL sodium citrate tribasic as a pH modifier; (g) 1 mg/mL potassium sorbate as a preservative agent; (h) 886.333 mg/mL sorbitol syrup n.c. 70% as a sweetening agent; and (i) purified water as a solvent q.s. to 1 mL.

In another embodiment, particularly suitable for a 5 mL adult formulation, the formulations comprise from 50 to 70 mg/mL netupitant or a pharmaceutically acceptable salt thereof (based on the weight of the free base), from 0.075 to 0.125 mg/mL palonosetron or a pharmaceutically acceptable salt thereof (based on the weight of the free base), from 2 to 3 mg/mL xanthan gum, from 800 to 950 mg/mL sorbitol syrup n.c. 70%, and from 0.5 to 1.5 mg/mL potassium sorbate.

In another embodiment particularly suitable for a 5 mL adult formulation the formulations comprise from 50 to 70 mg/mL netupitant or a pharmaceutically acceptable salt thereof (based on the weight of the free base), from 0.075 to 0.125 mg/mL palonosetron or a pharmaceutically acceptable salt thereof (based on the weight of the free base), from 2.5 to 3.5 mg/mL xanthan gum, from 850 to 900 mg/mL sorbitol syrup n.c. 70%, and from 0.75 to 1.25 mg/mL potassium sorbate.

In another embodiment particularly suitable for a 5 mL adult formulation the formulation comprises: (a) 60 mg/mL netupitant free base; (b) 0.1 mg/mL palonosetron HCl; (c) 50 mg/mL glycerin 98%; (d) 3 mg/mL xanthan gum; (e) 2 mg/mL citric acid anhydrous as a pH modifier; (f) 13.75 mg/mL sodium citrate tribasic as a pH modifier; (g) 1 mg/mL potassium sorbate as a preservative agent; (h) 886.333 mg/mL sorbitol syrup n.c. 70% as a sweetening agent; and (i) purified water as a solvent q.s. to 1 mL.

In one embodiment particularly suitable for a 10 mL pediatric formulation the formulations of the current disclosure comprise from 25 to 35 mg/mL netupitant or a pharmaceutically acceptable salt thereof (based on the weight of the free base), from 0.125 to 0.175 mg/mL palonosetron or a pharmaceutically acceptable salt thereof (based on the weight of the free base) (based on the weight of the free base), from 2 to 3 mg/mL xanthan gum, from 800 to 950 mg/mL sorbitol syrup n.c. 70%, and from 0.5 to 1.5 mg/mL potassium sorbate.

In another embodiment particularly suitable for a 10 mL pediatric formulation the formulations comprise from 25 to 35 mg/mL netupitant or a pharmaceutically acceptable salt thereof (based on the weight of the free base), from 0.125 to 0.175 mg/mL palonosetron or a pharmaceutically acceptable salt thereof (based on the weight of the free base), from 2.5 to 3.5 mg/mL xanthan gum, from 850 to 900 mg/mL sorbitol syrup n.c. 70%, and from 0.75 to 1.25 mg/mL potassium sorbate.

In one embodiment particularly suitable for a 10 mL pediatric formulation the composition comprises: (a) 60 mg/mL netupitant free base; (b) 0.15 mg/mL palonosetron HCl; (c) 50 mg/mL glycerin 98%; (d) 3 mg/mL xanthan gum; (e) 2 mg/mL citric acid anhydrous as a pH modifier; (f) 13.75 mg/mL sodium citrate tribasic as a pH modifier; (g) 1 mg/mL potassium sorbate as a preservative agent; (h) 886.333 mg/mL sorbitol syrup n.c. 70% as a sweetening agent; and (i) purified water as a solvent q.s. to 1 mL.

The formulations of the current disclosure are useful for obtaining a complete administration of the active ingredients to the patients. The formulations of the current disclosure comprising palonosetron or a pharmaceutically acceptable salt thereof and netupitant or a pharmaceutically salt thereof are contained in the single liquid dosage form in a stable combination avoiding any sedimentation effect, useful for the packaging as below in the present disclosure.

In another embodiment the manufacturing process to produce the formulation of the current disclosure is carried out in a manner that reduces the risk of foaming, poor API homogeneity, and incorrect dosing. In one embodiment, at the end of the bulk preparation, the suspension is kept under continuous stirring up to and during the filling process to avoid foam separation that could impact the content uniformity of the finished product. The formulation can be quite structured and viscous and prone to incorporate air during the process. If phase separation occurs, the formed foam can be enriched with palonosetron but not netupitant, leading to a final filled product with an incorrect ratio of netupitant to palonosetron. In order to avoid phase separation, the bulk is kept under stirring at the end of preparation and during the filling process.

Thus, in another embodiment the invention provides a method of manufacturing an orally administered antiemetic composition in a mixed suspension/solution solvent system comprising:

a) making a bulk formulation comprising from 0.01 to 0.2 mg/mL palonosetron or a pharmaceutically acceptable salt thereof (based on the weight of the free base) in a dissolved state and from 10 to 100 mg/mL of netupitant or a pharmaceutically acceptable salt thereof (based on the weight of the free base) in a solid suspended state; and b) filling the bulk formulation into a plurality of unit dose packages while continuously stirring the formulation to minimize or prevent foaming.

In one embodiment the bulk formulation comprises a solvent system in which the netupitant or pharmaceutically acceptable salt thereof is insoluble but homogenously suspended and the palonosetron or pharmaceutically acceptable salt thereof is soluble comprising water, one or more miscibilized wetting agents, one or more miscibilized suspending agents, one or more pH modifiers optionally one or more miscibilized sweetening agents, and optionally one or more miscibilized preservatives.

Another embodiment comprises filling about 10 mL of the bulk formulation into each unit dose package comprising 300 mg of netupitant or a pharmaceutically acceptable salt thereof at a concentration of 30 mg/mL, and 0.5 mg of palonosetron or a pharmaceutically acceptable salt thereof at a concentration of 0.05 mg/mL, wherein the doses and concentrations are based on the free form of the netupitant and palonosetron.

Another embodiment comprises filling about 5 mL of the bulk formulation into each unit dose package comprising 300 mg of netupitant or a pharmaceutically acceptable salt thereof at a concentration of 60 mg/mL, and 0.5 mg of palonosetron or a pharmaceutically acceptable salt thereof at a concentration of 0.1 mg/mL, wherein the doses and concentrations are based on the free form of the netupitant and palonosetron.

Another embodiment comprises filling about 10 mL of the bulk formulation into each unit dose package comprising 300 mg of netupitant or a pharmaceutically acceptable salt thereof at a concentration of 30 mg/mL, and 1.5 mg of palonosetron or a pharmaceutically acceptable salt thereof at a concentration of 0.15 mg/mL, wherein the doses and concentrations are based on the free form of the netupitant and palonosetron.

Packaging

Exemplary packaging for the liquid unit dosage forms includes pouches (e.g. liquid stick packs and sachets), plastic vials, glass vials, plastic tubes that are either consumed as-is, diluted in water prior to administration, or consumed as-is followed by the consumption of a liquid chaser. The packaging material in contact with the liquid formulation can be made from any suitable plastic that imparts stability to the formulation and excludes the transmission of substances either from or into the liquid formulation. Examples of materials suitable for the packaging include glass, polyester, polypropylene, polyethylene and polyethylene terephthalate (PET). In some embodiments the inner surface of the container comprises glass, polyester, polypropylene, or polyethylene.

In some embodiments a laminate is used to form the packaging. The materials used to construct the laminate sheet can be any that are customary in the art, such as polyester, polypropylene, polyethylene and polyethylene terephthalate (PET). In some embodiments the laminate comprises a layer of aluminum foil. Exemplary laminates include PET/ALU/PE 23/20/50 microns and PET/ALU/PE 12/9/50 microns.

The pouches are preferably made from one or two sheets of laminate configured to define an interior void sealed around its periphery. Examples of suitable designs for pouches are described, for example in US 2015/0144518A1 and US20030168375A1. Suitable laminates for pouches or other possible packaging can also be purchased from companies such as for example Unette Corporation (Randolph New Jersey), Amcor 360 Packaging Solutions (Melbourne Australia).

In some embodiments of the current disclosure, pouches are linear to avoid formation of any shoulder on the top that might cause the formulations to be blocked inside and impeding the complete recovery of the formulation and complete administration of the drug.

The packaging of the current disclosure can impart stability to the overall dosage form. In some embodiments, the packaged composition comprises less than about 1% or 0.5% total impurities. In another embodiment the formulation of the present invention has less than about 1% or 0.5% total impurities after storage at 40° C.±2° C. and 75% RH±5% RH for three or six months. In another embodiment the formulation of the present invention has less than about 0.5% total impurities after storage at 25° C.±2° C. and 60% RH±5% RH for nine months.

The packaging of the current disclosure provides an easier oral administration. In one embodiment the packaging is a single packaging for a single dosage unit, and it allows the direct administration in the mouth of the patient.

The packaging and the oral liquid antiemetic composition formulated in a mixed suspension/solution solvent system provides an improved compliance for the patients.

The improvement of compliance is especially useful for patients with difficulties in swallowing oral solid formulation such as, for example, patients suffering from head and neck tumors as well as oncologic patients with swallowing problems or dysphagia because of side effects of certain treatments as chemotherapy and/or radiotherapy. For example, people who have mouth sores (mucositis) due to chemotherapy or radiation therapy to the head and neck may have pain when swallowing and an easier administration of a liquid composition would be highly beneficial.

In another embodiment, the packaging of the current disclosure allows the full recovery of the dose and a maximized administration of the product. A maximized administration of the product will in turn ensure an optimized effect for the patient.

In some other embodiments the overfill can be about 1 mL for the 10 mL dose and about 0.5 mL for the 5 mL dose.

Methods of Treatment

In one embodiment the disclosure provides a method of preventing chemotherapy induced nausea and vomiting in a human patient in need thereof comprising orally administering to the patient an antiemetic composition in a mixed suspension/solution solvent system comprising palonosetron or a pharmaceutically acceptable salt thereof and netupitant or a pharmaceutically acceptable salt thereof together in a single liquid dosage form.

In another embodiment the disclosure provides a method of preventing chemotherapy induced nausea and vomiting in a human patient in need thereof comprising orally administering to the patient of about 300 mg of netupitant or pharmaceutically acceptable salt thereof (based on the weight of the free base) and about 0.5 mg palonosetron or pharmaceutically acceptable salt thereof (based on the weight of the free base) from any suitable formulation and/or packaging of the present disclosure.

In another embodiment, the disclosure provides a method of preventing chemotherapy induced nausea and vomiting in a human pediatric patient in need thereof comprising orally administering to the patient an antiemetic composition in a mixed suspension/solution solvent system comprising palonosetron or a pharmaceutically acceptable salt thereof and netupitant or a pharmaceutically acceptable salt thereof together in a single liquid dosage form.

approximately 45 mg/g and buffered with citrate salts. The following tests were performed:

- Appearance and taste of the suspensions
- Syringability, by testing the ease with which the required amount of product is drawn using a bottle plug and a graduated syringe
- Physical stability of the suspension: absence of sedimentation/cake formation during one week storage; re-suspension evaluation after gentle shaking
- pH between 5,0-6,0 was checked during storage to ensure not rheology changes that would adversely affect product performance and to maintain taste.

The compositions of the trials are summarized in Table 1:

TABLE 1

| | 199 | 182 | 179 | 174 | 180 | 177 | 187 | 191 | 185 | 197 | 198 |
|---|---|---|---|---|---|---|---|---|---|---|---|
| Netupitant Micronized | 4.500 | 4.500 | 4.500 | 4.500 | 4.500 | 4.500 | 4.500 | 4.500 | 4.500 | 4.500 | 4.500 |
| Sorbitol 70% | | | | | | | | | | 50.0 | 50.0 |
| Glycerin 98% | | 5.0 | 5.0 | | 5.0 | 5.0 | | | 5.0 | 5.0 | 5.0 |
| Xanthan_Gum (Xantural_75) | 0.300 | 0.200 | 0.300 | | | | | | | 0.300 | |
| Citric Acid Anhydrous | 0.200 | 0.200 | 0.200 | 0.200 | 0.200 | 0.200 | 0.200 | 0.200 | 0.200 | 0.200 | 0.200 |
| Sodium_Citrate Tribasic | 1.375 | 1.375 | 1.375 | 1.375 | 1.375 | 1.375 | 1.375 | 1.375 | 1.375 | 1.375 | 1.375 |

In another embodiment, the disclosure provides a method of preventing chemotherapy induced nausea and vomiting in a human pediatric patient in need thereof comprising orally administering to the patient of about 300 mg of netupitant or pharmaceutically acceptable salt thereof (based on the weight of the free base) and about 1.5 mg palonosetron or pharmaceutically acceptable salt thereof (based on the weight of the free base) from any suitable formulation and/or packaging of the present disclosure. Particularly suitable pediatric age ranges include 3-18 years and 3-12 years.

In a further embodiment, the method further comprises administering highly emetogenic chemotherapy ("HEC") or moderately emetogenic chemotherapy ("MEC") within 2 hours of administering the netupitant and palonosetron. For definitions of HEC and MEC, please refer to A Pocket Guide To EMETOGENICITY OF CHEMOTHERAPY REGIMENS Version 2019, published by Helsinn Healthcare SA (https://hospitalhealthcare.com/wpcontent/uploads/2020/09/HEL85_bookletEMESI_UNBRAND ED_191219.pdf).

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated and are intended to be purely exemplary of the disclosure and are not intended to limit the scope of what the inventors regard as their invention.

Example 1: Trials to Obtain a Suitable and Physical-Chemical Stable Suspension In order to select the most suitable suspending and wetting agents, a matrix of trials was designed and carried out. Each trial was set at a Netupitant concentration of All the preparations appeared as white, opaque, smooth suspensions, without lumps. Dose preparation trials were performed, to check the actual syringability of the product: all the suspensions were easily withdrawn from the bottle using the proper plug and graduated syringe. The preparations containing Xanthan gum remained stable and showed an absence of sedimentation after 30 days storage at room temperature. Preparations with Xanthan Gum were also characterized by a quick and complete hydration of the polymer that allows a rapid and simple manufacturing process.

Suspensions were also prepared using Carboxymethyl Cellulose. All of these suspensions showed separation (sedimentation) after about 20 or 30 days of storage but could be easily resuspended by gentle shaking. A pH of 5.0-6.0 was obtained with citrate salts and its value appeared stable during storage (tested after one week storage).

Example 2. Stability Study of Oral Suspension

An oral formulation was prepared according to the quali/quantitative recipe in Table 2 and tested for stability according to ICH Q1A(R2), Stability Testing of New Drug Substances and Products (November 2003). The stability results for an amber glass vial type III 10 mL, with a cap of neutral polymer and containing 10 mL of oral suspension are reported in Tables 3 and 4.

TABLE 2

| Ingredients | Function | mg/10 mL | mg/mL |
|---|---|---|---|
| Netupitant Micronized* | API | 300.00 | 30.00 |
| Palonosetron HCl** | API | 1.50 | 0.15 |
| Glycerin 98% | Wetting agent | 500.00 | 50.00 |
| Xanthan gum | Suspending agent | 30.00 | 3.00 |
| Citric acid anhydrous | pH modifier | 20.00 | 2.00 |
| Sodium citrate tribasic | pH modifier | 137.5 | 13.75 |

TABLE 2-continued

| Ingredients | Function | mg/10 mL | mg/mL |
|---|---|---|---|
| Potassium Sorbate | Preservative agent | 10.00 | 1.00 |
| Sorbitol Syrup n.c. 70% | Sweetening agent | 8863.33 | 886.333 |
| Purified Water | Solvent | 2215.83 | 221.583 |

*Netupitant free base

**Concentration based on weight of free palonosetron

TABLE 3

| (25° C./60% R.H.) | | | | | |
|---|---|---|---|---|---|
| Test | Time Zero | 3 months | 6 months | 12 months | 24 months |
| White to off-white homogeneous suspension | C | C | C | C | C |
| pH | 5.6 | 5.6 | 5.7 | 5.7 | 5.7 |
| Viscosity | 2920 cPs | 2808 cPs | 2792 cPs | 2848 cPs | 2792 cPs |
| Density at 20° C. | 1.239 | 1.243 | 1.244 | 1.239 | 1.240 |
| Uniformity of mass | C | TNP | C | C | C |
| Absence of crystals | C | C | C | C | C |
| Assay (HPLC)-Netupitant | 103.7% | 103.4% | 101.7% | 102.8% | 103.1% |
| Any unspecified degradation product | <0.05% | <0.05% | <0.05% | <0.05% | <0.05% |
| Total degradation products | <0.05% | <0.05% | <0.05% | <0.05% | <0.05% |
| Assay (HPLC)-Palonosetron | 102.0% | 104..4% | 101.1% | 99.3% | 103.4% |
| Impurity 07-Palo | 0.18% | ND | ND | 0.17% | 0.10% |
| Impurity 09-Palo | 0.05% | 0.06% | 0.19% | 0.22% | 0.10% |
| Impurity 08-Palo-D1 | ND | <0.05% | ND | ND | ND |
| Any unspecified degradation product | <0.05% | 0.07% | <0.05% | 0.08% | <0.05% |
| Total degradation products | 0.23% | 0.13% | 0.19% | 0.60% | 0.20% |
| Assay (HPLC)-Potassium sorbate | 103.7% | 99.2% | 100.2% | 100.6% | 94.9% |

TABLE 4

| (40° C./75% R.H.) | | | | |
|---|---|---|---|---|
| Test | Time Zero | 1 month | 3 months | 6 months |
| White to off-white homogeneous suspension | C | C | C | C |
| pH | 5.6 | 5.7 | 5.7 | 5.8 |
| Viscosity | 2920 cPs | 2740 cPs | 2616 cPs | 2776 cPs |
| Density at 20° C. | 1.239 | 1.242 | 1.243 | 1.244 |
| Uniformity of mass | C | TNP | TNP | C |
| Absence of crystals | C | C | C | C |
| Assay (HPLC)-Netupitant | 103.7% | 103.2% | 103.3% | 102.4% |
| Any unspecified degradation product | <0.05% | <0.05% | <0.05% | <0.05% |

TABLE 4-continued

| (40° C./75% R.H.) | | | | |
|---|---|---|---|---|
| Test | Time Zero | 1 month | 3 months | 6 months |
| Total degradation products | <0.05% | <0.05% | <0.05% | <0.05% |
| Assay (HPLC)-Palonosetron | 102.0% | 104.0% | 105.7% | 101.6% |
| Impurity 07-Palo | 0.18% | <0.05% | ND | ND |
| Impurity 09-Palo | 0.05% | 0.08% | 0.06% | 0.27% |
| Impurity 08-Palo-D1 | ND | ND | <0.05% | 0.10% |
| Any unspecified degradation product | <0.05% | <0.05% | <0.05% | <0.05% |
| Total degradation products | 0.23% | 0.08% | 0.06% | 0.37% |
| Assay (HPLC)-Potassium sorbate | 103.7% | 96.2% | 99.1% | 99.7% |

Example 3. Other Oral Suspensions

Other formulations are reported in Tables 5 and 6, wherein Table 5 reports the composition of an exemplary 10 mL dose and Table 6 reports the composition of an exemplary 5 mL dose. The stability results of this formulation packed in PET/Alu/PE stick pack are reported in Table 7 and 8 for 25° C./60% RH and 40° C./75% RH respectively:

TABLE 5

| | mg/mL | mg/10 mL |
|---|---|---|
| Netupitant micronized | 30 | 300 |
| Palonostron HCl* | 0.056 | 0.56 |
| Glycerin 98% | 50 | 500 |
| Xanthan gum | 3 | 30 |
| Citric acid anhydrous | 2 | 20 |
| Sodium citrate tribasic | 13.75 | 137.5 |
| Potassium sorbate | 1 | 10 |
| Sorbitol Syrup n.c. 70% | 886.33 | 8863.3 |
| Purified Water | up to 1 mL | up to 10 mL |

*concentration based on weight of HCl salt

TABLE 6

| | mg/mL | mg/5 mL |
|---|---|---|
| Netupitant micronized | 60 | 300 |
| Palonosetron HCl* | 0.112 | 0.56 |
| Glycerin 98% | 50 | 500 |
| Xanthan gum | 3 | 30 |
| Citric acid anhydrous | 2 | 20 |
| Sodium citrate tribasic | 13.75 | 137.5 |
| Potassium sorbate | 1 | 10 |
| Sorbitol Syrup n.c. 70% | 886.33 | 8863.3 |
| Purified Water | up to 1 mL | up to 5 mL |

*concentration based on weight of HCl salt

TABLE 7

| Test | Specification | T0 | 1 mo | 2 mo | 3 mo | 6 mo | 9 mo |
|---|---|---|---|---|---|---|---|
| Appearance | White homogeneous suspension | | | | | | |
| pH | Report result | 5.7 | 5.8 | 5.7 | 5.7 | 5.8 | 5.7 |
| Density | Report result | 1.242 | 1.244 | 1.242 | 1.245 | 1.240 | 1.245 |
| Assay (HPLC) Netupitant | 95.0-105.0% of label claim | 103.5% | 104.0% | 104.3 | 104.7% | 104.3% | 104.7% |
| Any unspecified degradation products: | NMT 0.2% | <0.05% | <0.05% | <0.05% | 0.07% | <0.05% | <0.05% |
| Total degradation products | NMT 1.0% | <0.05% | <0.05% | <0.05% | 0.07% | <0.05% | <0.05% |
| Assay (HPLC) Palonosetron | 95.0-105.0% of label claim | 101.1% | 104.0% | 103.2% | 104.7% | 103.2% | 104.1% |
| 08-Palo-D1 | NMT 1.0% | ND | 0.18% | 0.31% | 0.07% | 0.11% | 0.23% |
| Any unspecified degradation products: | | | | | | | |
| RRT 0.23 | NMT 1.0% | 0.07% | <0.05% | <0.05% | <0.05% | <0.05% | <0.05% |
| RRT 0.25 | | 0.06% | <0.05% | <0.05% | <0.05% | <0.05% | <0.05% |
| RRT 0.29* | | 0.17% | 0.25% | 0.34% | 0.36% | 1.26% | 1.35% |
| RRT 0.30* | | 0.13% | 0.13% | 0.17% | 0.20% | 0.40% | 0.25% |
| RRT 0.34 | | <0.05% | <0.05% | <0.05% | <0.05% | 0.12% | 0.07% |
| RRT 0.36 | | <0.05% | <0.05% | <0.05% | <0.05% | 0.21% | 0.11% |
| RRT 0.39 | | <0.05% | <0.05% | <0.05% | <0.05% | 0.19% | 0.12% |
| RRT 0.48 | | 0.07% | <0.05% | <0.05% | <0.05% | 0.20% | 0.21% |
| RRT 0.57 | | <0.05% | <0.05% | <0.05% | <0.05% | <0.05% | 0.10% |
| RRT 0.68 | | <0.05% | 0.07% | <0.05% | <0.05% | 0.08% | 0.08% |
| RRT 0.71 | | <0.05% | <0.05% | <0.05% | <0.05% | 0.05% | 0.17% |
| RRT 0.84 | | <0.05% | <0.05% | <0.05% | <0.05% | 0.07% | 0.08% |
| RRT 0.94 | | <0.05% | <0.05% | <0.05% | <0.05% | <0.05% | <0.05% |
| RRT 0.96 | | 0.19% | 0.17% | 0.34% | 0.40% | 0.20% | 0.39% |
| (07-Palo) | | 0.15% | 0.23% | 0.24% | 0.23% | 0.20% | 0.22% |
| RRT 0.97 | | <0.05% | <0.05% | <0.05% | <0.05% | 0.28% | 0.09% |
| (09-Palo) | | 0.10% | <0.05% | <0.05% | <0.05% | 0.11% | 0.13% |
| RRT 1.07 | | 0.19% | <0.05% | <0.05% | <0.05% | 0.18% | 0.19% |
| RRT 1.13 | | | | | | | |
| RRT 1.19 | | | | | | | |
| Total degradation products | NMT 3.0% | 1.1% | 1.0% | 1.4% | 1.3% | 3.7% | 3.8% |
| Assay (HPLC) Potassium Sorbate | Report result | 103.2% | 100.2% | 101.5% | 95.0% | 99.0% | 101.0% |

45

TABLE 8

| Test | Specification | T0 | 1 mo | 2 mo | 3 mo | 6 mo |
|---|---|---|---|---|---|---|
| Appearance | White homogeneous suspension | | | | | |
| pH | Report result | 5.7 | 5.7 | 5.8 | 5.7 | 5.7 |
| Density | Report result | 1.242 | 1.244 | 1.241 | 1.242 | 1.245 |
| Assay (HPLC) Netupitant | 95.0-105.0% of label claim | 103.5% | 104.9% | 104.5% | 104.6% | 104.3% |
| Related substances Netupitant (HPLC)-(reporting limit ≥0.05%) | | | | | | |
| Any unspecified degradation products: | NMT 0.2% | <0.05% | <0.05% | <0.05% | 0.09% | 0.05% |
| Total degradation products | NMT 1.0% | <0.05% | <0.05% | <0.05% | 0.09% | 0.05% |
| Assay (HPLC) Palonosetron | 95.0-105.0% of label claim | 101.1% | 103.7% | 103.2% | 102.9% | 102.6% |

TABLE 8-continued

| Test | Specification | T0 | 1 mo | 2 mo | 3 mo | 6 mo |
|---|---|---|---|---|---|---|
| Related substances Palonosetron (HPLC)-(reporting limit ≥0.05%) | | | | | | |
| 08-Palo-D1 | NMT 1.0% | ND | 0.23% | 0.25% | 0.14% | 0.32% |
| Any unspecified degradation products: | | | | | | |
| RRT 0.23 | NMT 1.0% | 0.07% | <0.05% | <0.05% | <0.05% | <0.05% |
| RRT 0.25 | | 0.06% | <0.05% | <0.05% | <0.05% | <0.05% |
| RRT 0.29* | | 0.17% | 0.57% | 0.78% | 0.97% | 1.97% |
| RRT 0.30* | | 0.13% | 0.06% | <0.05% | 0.08% | 0.97% |
| RRT 0.33 | | <0.05% | <0.05% | 0.05% | <0.05% | <0.05% |
| RRT 0.34 | | <0.05% | <0.05% | 0.09% | <0.05% | <0.05% |
| RRT 0.56 | | <0.05% | <0.05% | <0.05% | <0.05% | 0.15% |
| RRT 0.68 | | 0.07% | <0.05% | <0.05% | <0.05% | <0.05% |
| RRT 0.84 | | <0.05% | <0.05% | <0.05% | <0.05% | 0.09% |
| RRT 0.94 | | <0.05% | 0.07% | <0.05% | <0.05% | <0.05% |
| RRT 0.96 (07-Palo) | | 0.19% | 0.18% | 0.33% | 0.35% | 0.24% |
| RRT 0.97 (09-Palo) | | 0.15% | 0.23% | 0.25% | 0.22% | 0.13% |
| RRT 1.13 | | 0.10% | <0.05% | <0.05% | <0.05% | 0.08% |
| RRT 1.19 | | 0.19% | <0.05% | <0.05% | <0.05% | 0.17% |
| Total degradation products | NMT 3.0% | 1.1% | 1.3% | 1.8% | 1.8% | 4.1% |
| Assay (HPLC) Potassium Sorbate | Report result | 103.2% | 98.6% | 98.4% | 96.6% | 90.9% |

Example 4. Stability Xanthan Gum

TABLE 9

| Trial formulation | pH at $T_0$ | pH after 7 days |
|---|---|---|
| Xanthan Gum 0.3% | 5.55 | 5.54 |
| Xanthan Gum 0.2% + glycerin | 5.56 | 5.54 |
| Xanthan Gum 0.3% + Glycerin | 5.54 | 5.56 |
| Xanthan Gum 0.3% + Glycerin (with sorbitol) | 5.60 | 5.59 |
| Xanthan Gum 0.3% + poloxamer | 5.56 | 5.57 |
| Xanthan Gum 0.3% + propylene glycole | 5.63 | 5.64 |
| Xanthan Gum 0.4% + glycerin | 5.57 | 5.54 |
| Polycarbphil 0.3% | 5.49 | settled |
| Polycarbphil 0.2% + glycerin | 5.61 | settled |
| Polycarbphil 0.3% + Glycerin | 5.52 | settled |
| Polycarbphil 0.3% + poloxamer | 5.52 | settled |
| Polycarbphil 0.3% + propylene glycole | 5.63 | settled |
| Polycarbphil 0.4% + glycerin | 5.46 | settled |
| Na carbossimethyl cellulose 0.3% | 5.54 | 5.52 |
| Na carbossimethyl cellulose 0.2% + glycerin | 5.56 | 5.55 |
| Na carbossimethyl cellulose 0.3% + Glycerin | 5.55 | 5.55 |
| Na carbossimethyl cellulose 0.3% + Glycerin (with sorbitol) | 5.59 | settled |
| Na carbossimethyl cellulose 0.3% + poloxamer | 5.54 | 5.56 |
| Na carbossimethyl cellulose 0.3% + propylene glycole | 5.61 | 5.63 |
| Na carbossimethyl cellulose 0.4% + glycerin | 5.57 | 5.53 |

As can be seen, formulations with Xanthan Gum consistently remained stable in terms of pH and sedimentation.

Other Embodiments

Other embodiments and embodiments of the disclosure will be apparent to those skilled in the art from consideration of the specification and practice of the disclosure disclosed herein. It is intended that the specification and examples be considered as exemplary only, with a true scope and spirit of the invention being indicated by the following claims.

The invention claimed is:

1. An orally administered antiemetic composition in a mixed suspension/solution solvent system comprising:

a) from 0.01 to 0.2 mg/mL palonosetron or a pharmaceutically acceptable salt thereof (based on the weight of the free base) in a dissolved state and from 10 to 100 mg/mL of netupitant or a pharmaceutically acceptable salt thereof (based on the weight of the free base) in a solid suspended state; and b) a solvent system in which the netupitant or pharmaceutically acceptable salt thereof is insoluble and in a solid state but homogenously suspended and the palonosetron or pharmaceutically acceptable salt thereof is soluble and in a dissolved state comprising water, one or more miscibilized wetting agents, one or more miscibilized suspending agents, one or more pH modifiers, optionally one or more miscibilized sweetening agents, and optionally one or more miscibilized preservatives.

2. The composition of claim 1, wherein the solvent system comprises one or more miscibilized sweetening agents; and one or more miscibilized preservatives.

3. The composition of claim 1, wherein the palonosetron is present as palonosetron HCl and the netupitant is present as the free base.

4. The composition of claim 1, wherein the netupitant is present as a free base and has a particle size distribution defined by a d(50) of 1-8 μm and a d(90) of not more than 24 μm or a d(50) of 2-4 μm and a d(90) of not more than 12 μm.

5. The composition of claim 1, having a pH of from 4 to 7 or from 5 to 6.

6. The composition claim 1, comprising 30 mg/mL of netupitant free base and 0.056 mg/mL of palonosetron HCl.

7. The composition of claim 1, wherein the wetting agent is selected from the group consisting of glycerin, propylene glycol, polyethylene glycol, ethanol, and combinations thereof.

8. The composition of claim 1, comprising from 25 to 100 mg/mL, from 35 to 75 mg/mL, or 50 mg/mL glycerin as a wetting agent.

9. The composition of claim 1, wherein the suspending agent is selected from the group consisting of cellulose derivatives, acacia, xanthan gum, and combinations thereof.

10. The composition of claim 1, comprising from 2 to 4 mg/mL, from 2.5 to 3.5 mg/mL, or 3 mg/mL xanthan gum as a suspending agent.

11. The composition of claim 1, wherein the pH modifier is selected from the group consisting of citric acid anhydrous and sodium citrate tribasic and combinations thereof.

12. The composition of claim 1, comprising:

a) from 25 to 100 mg/mL, from 35 to 75 mg/mL, or 50 mg/mL glycerin; and b) from 2 to 4 mg/mL, from 2.5 to 3.5 mg/mL, or 3 mg/mL xanthan gum.

13. The composition of claim 1, comprising:

a) from 2 to 4 mg/mL, from 2.5 to 3.5 mg/mL, or 3 mg/mL xanthan gum;

b) from 800 mg/mL to 950 mg/mL, from 850 to 900 mg/mL, or 886.333 mg/mL sorbitol syrup n.c. 70%; and c) from 0.5 to 1.5 mg/mL, from 0.75 to 1.25 mg/mL, or 1 mg/mL potassium sorbate.

14. A method of preventing chemotherapy induced nausea and vomiting in a human patient in need thereof comprising orally administering to the patient 300 mg of netupitant or pharmaceutically acceptable salt thereof (based on the weight of the free base) and 0.5 mg palonosetron or pharmaceutically acceptable salt thereof (based on the weight of the free base) from the composition of claim 1.

15. The method of claim 14, further comprising administering highly emetogenic chemotherapy or moderately emetogenic chemotherapy within 2 hours of administering the netupitant and palonosetron.

16. A method of manufacturing an orally administered antiemetic composition in a mixed suspension/solution solvent system comprising:

a) making a bulk formulation comprising from 0.01 to 0.2 mg/mL palonosetron or a pharmaceutically acceptable salt thereof (based on the weight of the free base) in a dissolved state and from 10 to 100 mg/mL of netupitant or a pharmaceutically acceptable salt thereof (based on the weight of the free base) in a solid suspended state; and b) filling the bulk formulation into a plurality of unit dose packages while continuously stirring the formulation to minimize or prevent foaming.

17. The method of claim 16, wherein the bulk formulation comprises a solvent system in which the netupitant or pharmaceutically acceptable salt thereof is insoluble but homogenously suspended and the palonosetron or pharmaceutically acceptable salt thereof is soluble comprising water, one or more miscibilized wetting agents, one or more miscibilized suspending agents, one or more pH modifiers, optionally one or more miscibilized sweetening agents, and optionally one or more miscibilized preservatives.

18. The method of claim 16, comprising filling about 10 mL of the bulk formulation into each unit dose package comprising 300 mg of netupitant or a pharmaceutically acceptable salt thereof at a concentration of 30 mg/mL, and 0.5 mg of palonosetron or a pharmaceutically acceptable salt thereof at a concentration of 0.05 mg/mL, wherein the doses and concentrations are based on the free form of the netupitant and palonosetron.

19. The method of claim 16, wherein the netupitant is present as a free base and has a particle size distribution defined by a d(50) of 1-8 μm and a d(90) of not more than 24 μm or a d(50) of 2-4 μm and a d(90) of not more than 12 μm.

20. The method of claim 16, wherein the netupitant is present as a free base and has a particle size distribution defined by a d(50) of 1-8 μm and a d(90) of not more than 24 μm or a d(50) of 2-4 μm and a d(90) of not more than 12 μm.

21. The composition of claim 1, wherein the netupitant is present as a free base and has a particle size distribution defined by a d(50) of less than about 8 μm.

* * * * *